United States Patent [19]
Pitesky

[11] Patent Number: 6,077,229
[45] Date of Patent: *Jun. 20, 2000

[54] ALLERGY TESTING APPARATUS

[76] Inventor: Isadore Pitesky, 4001 Linden Ave., Long Beach, Calif. 90807

[*] Notice: This patent is subject to a terminal disclaimer.

[21] Appl. No.: 09/181,694

[22] Filed: Oct. 27, 1998

Related U.S. Application Data

[63] Continuation-in-part of application No. 08/955,370, Oct. 21, 1997, Pat. No. 5,931,794.

[51] Int. Cl.⁷ ........................................ A61B 5/00
[52] U.S. Cl. ........................... 600/556; 604/46; 606/186
[58] Field of Search .................... 600/556; 604/46, 604/47, 173; 606/186

[56] References Cited

U.S. PATENT DOCUMENTS

| | | | |
|---|---|---|---|
| 2,522,309 | 9/1950 | Simon | 128/2 |
| 3,289,670 | 12/1966 | Krug et al. | 128/2 |
| 3,512,520 | 5/1970 | Cowan | 600/556 |
| 3,688,764 | 9/1972 | Reed | 600/556 |
| 3,921,804 | 11/1975 | Tester | 206/531 |
| 4,222,392 | 9/1980 | Brennan | 604/47 |
| 4,237,906 | 12/1980 | Havstad et al. | 600/556 |
| 4,292,979 | 10/1981 | Inglefield, Jr. et al. | 600/556 |
| 4,304,241 | 12/1981 | Brennan | 600/556 |
| 4,453,926 | 6/1984 | Galy | 604/47 |
| 4,607,632 | 8/1986 | Brennan et al. | 600/556 |
| 4,714,621 | 12/1987 | Gullberg | 427/2 |
| 4,802,493 | 2/1989 | Maganias | 600/556 |
| 4,863,023 | 9/1989 | Payne et al. | 600/556 |
| 5,154,181 | 10/1992 | Fishman | 600/556 |
| 5,417,683 | 5/1995 | Shiao | 606/1 |
| 5,538,134 | 7/1996 | Pitesky | 604/173 |
| 5,551,441 | 9/1996 | Pitesky | 600/556 |
| 5,605,160 | 2/1997 | Fishman | 600/556 |
| 5,692,518 | 12/1997 | Baker et al. | 128/743 |
| 5,735,288 | 4/1998 | Fishman | 600/556 |
| 5,746,700 | 5/1998 | Hsiao | 600/556 |
| 5,749,836 | 5/1998 | Hsiao | 600/556 |

OTHER PUBLICATIONS

Page 23 of United Laboratory Plastics catalog on Screw Cap Micro Tubes, Jan. 1997.

*Primary Examiner*—Cary O'Connor
*Assistant Examiner*—Charles Marmor, II
*Attorney, Agent, or Firm*—Fulwilder Patton Lee & Utecht, LLP

[57] ABSTRACT

An allergen testing pick for receipt in the open top end of a vial of allergen and including a neck for close fit with the top end of such vial. The pick includes a stem depending downwardly from such neck and is formed with a plurality of sharp tines. A device may be provided for receiving the vials and may be in the form of a plurality of individual modules releasably coupled together.

20 Claims, 8 Drawing Sheets

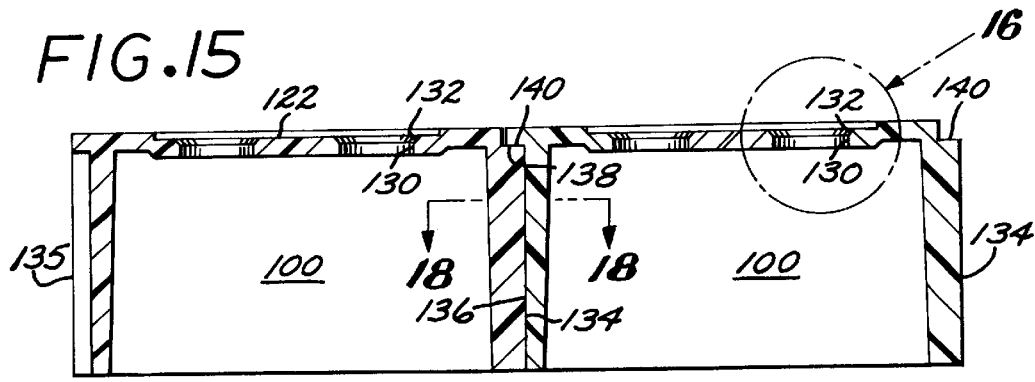
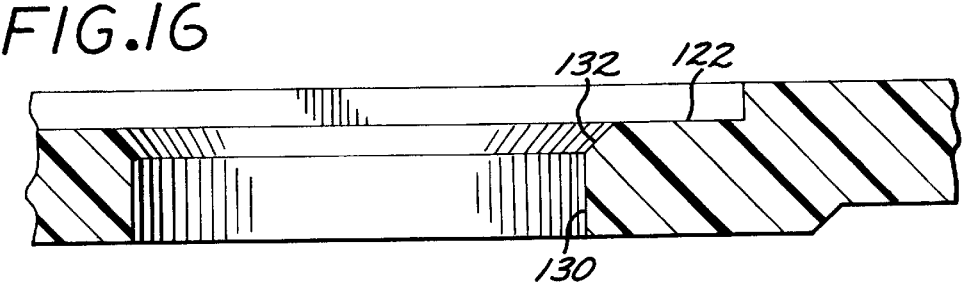
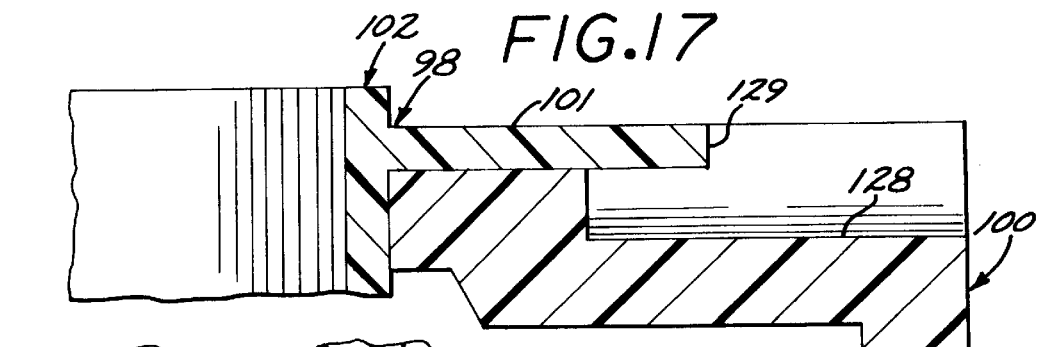
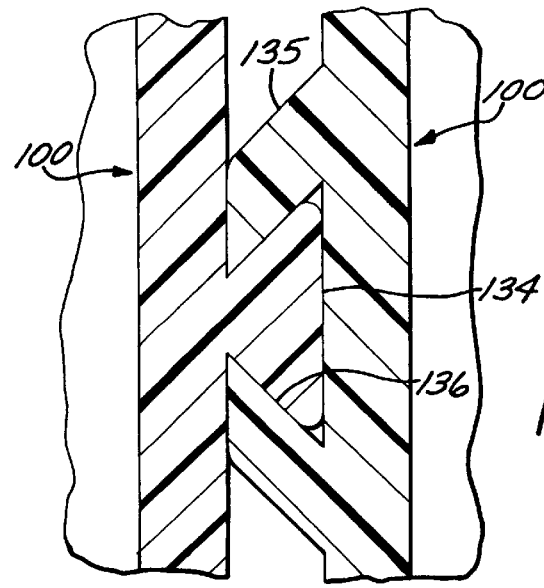

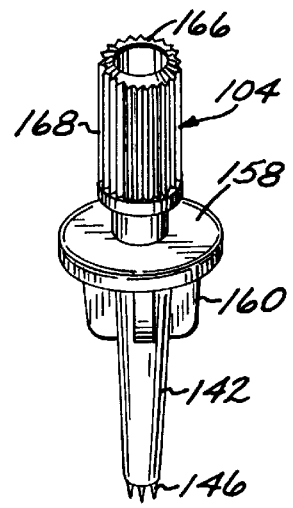
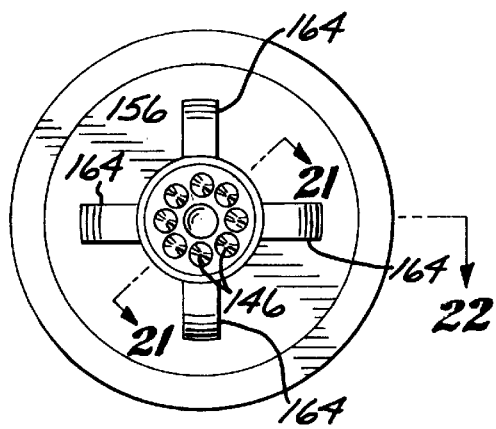
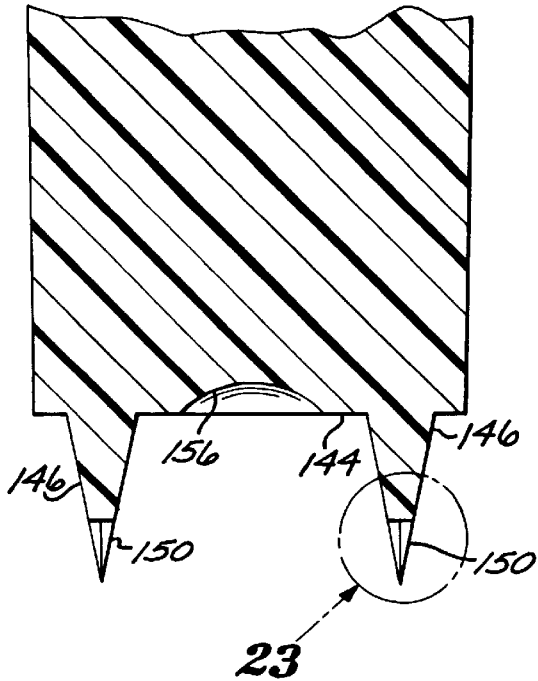
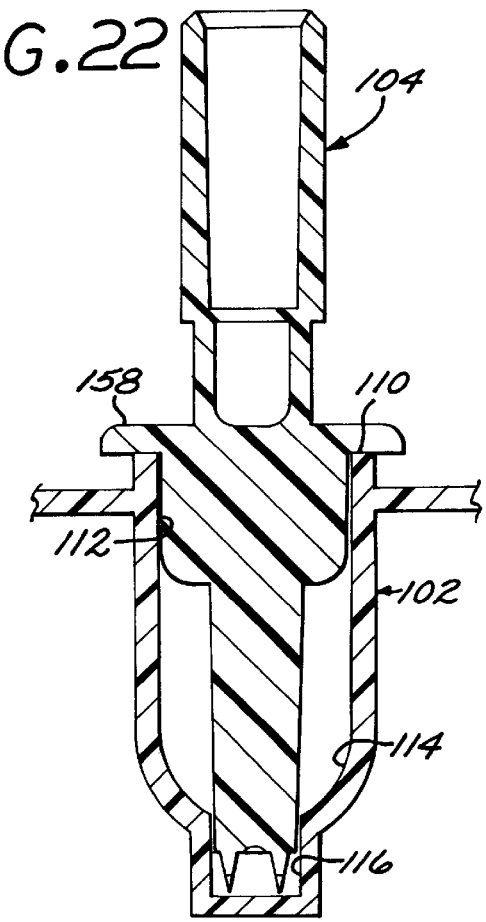

ALLERGY TESTING APPARATUS

BACKGROUND OF THE INVENTION

This application is a continuation-in-part of application Ser. No. 08/955,370, filed Oct. 21, 1997, now U.S. Pat. No. 5,931,794.

FIELD OF THE INVENTION

The present invention relates to a self loading and self sealing, disposable allergy testing apparatus.

DESCRIPTION OF THE PRIOR ART

Allergy testing involves subjecting a patient to a wide variety of different allergens to determine which allergens cause allergic reactions in the patient. Such testing requires that the respective allergens be applied beneath the surface of the patient's skin. Typically, the patient is first screened by superficial scratches or punctures with allergens to test for severe reactions. If there are no severe reactions, the patient may be subjected to intradermal tests with small bore needles. There are two methods of screening with an allergen application, the first being the puncture method and the second the abrasion method. Ideally an allergen applicator for screening should be capable of use in either the puncture or abrasion technique. The medical technician would then have the option to, if the puncture technique proves ineffective, perform the abrasion technique. The puncture method is accomplished by piercing the patient's skin with pointed prongs covered with a selected allergen. The second method, abrasion, involves abrading the skin by a scarifying device such as a sharp knife or chisel like instrument to introduce an allergen to the skin surface. Once one of these screening techniques have been completed for the allergens of interest without significant reaction, the patient is cleared for an intradermal test which typically involve introducing the allergen of interest by a hollow needle about ⅜ inch long on a syringe to be manipulated under the skin at an acute angle to the plane of the skin to strategically locate the distal end for injection of a highly diluted allergen.

Both the abrading and intradermal techniques can be satisfactorily performed only by technicians having considerable experience and sensitivity to the allergen used and the skin of the patient, as well as familiarity with the abrading tool. Different technicians performing the aforementioned screening tests oftentimes do not achieve the same results because the intensity and penetration of the abrasion and amount of allergen introduced into the skin varies from patient to patient and is highly dependent on the particular manner in which the technique is carried out. The degree of variation is compounded by the fact that different patients possess different skin thickness, toughness and sensitivity.

One device proposed for the delivery of allergen involves the use of a pick including a single, hollow cylindrical chisel to create capillary action when the chisel is submersed within the allergen. It is proposed that the hollow cylindrical bore would be effective to hold the proper amount of allergen. This form of allergen applicator can be found in U.S. Pat. No. 4,304,241. This device is limited to delivering allergen subcutaneously and cannot be used in the abrading mode. Also, because the device does not limit the depth of penetration of the chisel, dispensing the allergen to the proper depth within the patient's skin requires a certain degree of skill on the part of the technician.

Another device proposed by the prior art is a single tooth pick-like cylindrical stem formed at its bottom end with a bifurcated point to define a pair of blades. A device of this type has been manufactured by Lincoln Diagnostics under the trademark DUOPICK-TEST®. Such devices suffer the shortcoming that they are awkward to use, inconvenient to manipulate and, when placed uncovered in their respective wide mouth vials, tend to lay off at different angles from the vertical in a disorganized fashion. Moreover, with only two relatively blunt tines, the quantity of allergen which can be administered is limited. Additionally, since the vials fail to incorporate closures, the allergens are exposed to the air resulting in the introduction of air borne pathogens.

One prior art device, previously sold under the trademark DERMAPIK, incorporated an antigen assembly including a tray configured with upwardly opening wells dispersed thereabout and closed at their respective top ends by means of stoppers configured with a centrally disposed, severable bubble covering a small diameter entry passage. Thus, in practice, the technician could gain access to allergen stored in the vial by cutting off the bubble tip to create a small opening and inserting a small diameter stem of an applicator through the small opening. A device of this type is shown in my U.S. Pat. No. 4,237,906. While having enjoyed great commercial success, such a device suffers the shortcoming that removal of the bubble cap is time consuming, requires some degree of dexterity and can contribute to contamination of the allergen. Additionally, the relatively close interfitting relationship between the stem and entry opening requires relatively steady nerves on behalf of the technician and some degree of patience for inserting the stem into the passage.

One device proposed as a multiple-allergen screening and/or diagnostic kit includes different styles of injection devices, one having a beveled cannula constructed from a 15–25 gauge needle and the other having a clover leaf shaped plastic prong configured with an eyelet to hold the allergen. A device of this type is shown in U.S. Pat. No. 4,222,392 to Brennan. While possibly effective for intradermal application, the device shown is relatively expensive to manufacture and fails to provide an even effective means for holding the desired quantity of allergen necessary for a reliable screening test.

Other efforts led to the proposal of an allergy applicator including a stem formed on its working end with a plurality of axial tines having one or more axial stops interposed therebetween to limit penetration of such tines so they will not penetrate the epidermis. A device of this type is shown in U.S. Pat. No. 5,749,836 to Hsiao. While the device could possibly be somewhat effective for a scratch technique not requiring penetration below the epidermis, such a device would be ineffective in a true puncture technique.

In this regard, the applicator stem shown in my U.S. Pat. No. 4,237,906 incorporates a circular array of relatively short, pyramidal shaped teeth for abrading the patient's skin. Such teeth are of relatively wide cross section at their base and throughout a major portion of their respective axial lengths thus rendering them unacceptable for sufficiently deep penetration to apply antigens below the surface of the epidermis. Further, such teeth are not sized or arranged in such a manner as to provide for carrying of a sufficient quantity of allergen of the viscosity presently utilized in the medical field thus limiting its usage to technicians having some degree of experience and skill in performing the procedure.

Several devices have been developed which incorporate multiple picks to apply a plurality of allergens simultaneously at predetermined spaced apart locations on the patient's skin. However, because allergen is being applied simultaneously at several adjacent locations, the device must be pressed straight down and often rocked back and forth about the curved shape of the patient's skin in, for instance the arm area, and the individual applicators cannot be twisted about their own axes as is required in the abrasion mode. A device of this type may be problematic for use on patients having small diameter arms which do not provide skin having a sufficient extent of relatively flat surface for applying many allergens simultaneously. Devices of this type are shown in my U.S. Pat. No. 5,551,441, as well as in U.S. Pat. Nos. 2,522,309 and 5,154,181.

Still another device proposed includes a base having a set number of upwardly opening wells for receipt of individual picks covered collectively by a single removable cover or to be covered individually by separate well caps. A device of this type is shown in my U.S. Pat. No. 5,538,134. While this device provides convenient access to and secure sealing of the allergen, it fails to provide the convenience and flexibility of providing a holder adapted to receive different sets of vials of allergen which can be changed to accommodate the differing needs of various patients.

In effort to overcome the problems attendant the above-mentioned devices, I proposed in my U.S. application, Ser. No. 08/995,370, filed Oct. 21, 1997, and now U.S. Pat. No. 5,931,794, an allergy tray having large mouth, upwardly opening vials for receipt of individual picks having large diameter covers and downwardly depending stems terminating in individual thin conical tines arranged in a circular pattern. Such a device, while providing satisfactory results and having substantial commercial promise, poses the problem that the tray itself is relatively expensive to manufacture and the conical points on the tip of the tines do no have great structural integrity and fail to knife into the skin as effectively as they could.

The allergen, remaining in the vial, being expensive and sensitive to environmental exposure, should be conserved for subsequent application. Therefore, it is desirable that the allergen be stored in a container which can be easily sealed after use and which will collect the residual allergen for effective use in subsequent applications. It is desirable that the pick be constructed to facilitate extraction of the residual allergen from the container and to subsequently seal the container without requiring inordinate manual dexterity or the use of extraneous tools. Since it is often desirable to vary the number of allergens tested on any particular patient, it would be preferable to be able to easily vary the number and type of allergen containers in a set to provide the technician the flexibility of varying the number of allergens in such set.

Thus, there exists a need for an allergy testing device which is self sealing, self loading, and disposable with the proper quantity of allergen and which can be used for either a puncture application or abrasion application.

SUMMARY OF THE INVENTION

The allergy testing apparatus of the present invention is characterized by a tray apparatus having a plurality of wells therein for receiving individual applicator picks. Advantageously, the applicator includes a stem formed on its bottom extremity with a plurality of sharply pointed substantially conical tines. In practice, the shape of the penetration tip may take on the form of a thin sharp inverted pyramid to facilitate the molding procedure and forms diverging spreader facets which serve to promote initial penetration into the patient's skin. In use, the applicator pick is removed from the vial, thereby extracting a predetermined amount of allergen. The pointed tines are then used to either puncture or abrade the patient's skin, depositing the extracted allergen into the skin. The flat bottom of the shaft of the applicator pick from which the tines extend acts as a stop when the tines are puncturing the patient's skin, limiting penetration to a predetermined depth. In one embodiment, the center of the bottom of the applicator pick from which the tines project may be formed with a recess of a selected size to cooperate with the tines in holding a set amount of allergen.

The tray apparatus may include a plastic hollow box-like structure formed in its top wall with a rectangular recess extending about the majority of the area thereof and formed with spaced bores. A flat strip of plastic is nested downwardly in the recess and is formed with individual integral vials having large upwardly facing openings for receipt of a cap or cover integrated in the respective picks when the picks are inserted therein.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 15 is a sectional view, in enlarged scale, showing a pair of trays, as depicted in FIG. 12 locked together;

FIG. 16 is a detail view taken from circle 16 of FIG. 15; shown in enlarged scale;

FIG. 17 is a detail view, taken from circle 17 of FIG. 14, shown in enlarged scale;

FIG. 18 is a longitudinal sectional view, taken along line 18—18 of FIG. 15, in enlarged scale;

FIG. 19 is a perspective view of an alternate embodiment of an applicator pick of the present invention;

FIG. 20 is a bottom plan view, shown in enlarged scale, of the applicator pick of FIG. 20;

FIG. 21 is a transverse sectional view, taken along line 21—21 in FIG. 20, shown in enlarged scale and inverted;

FIG. 22 is a sectional view, taken along line 22—22 of FIG. 20, in reduced scale, inverted, showing the pick installed in a well;

DETAILED DESCRIPTION OF THE PREFERRED EMBODIMENT

Figure 1:
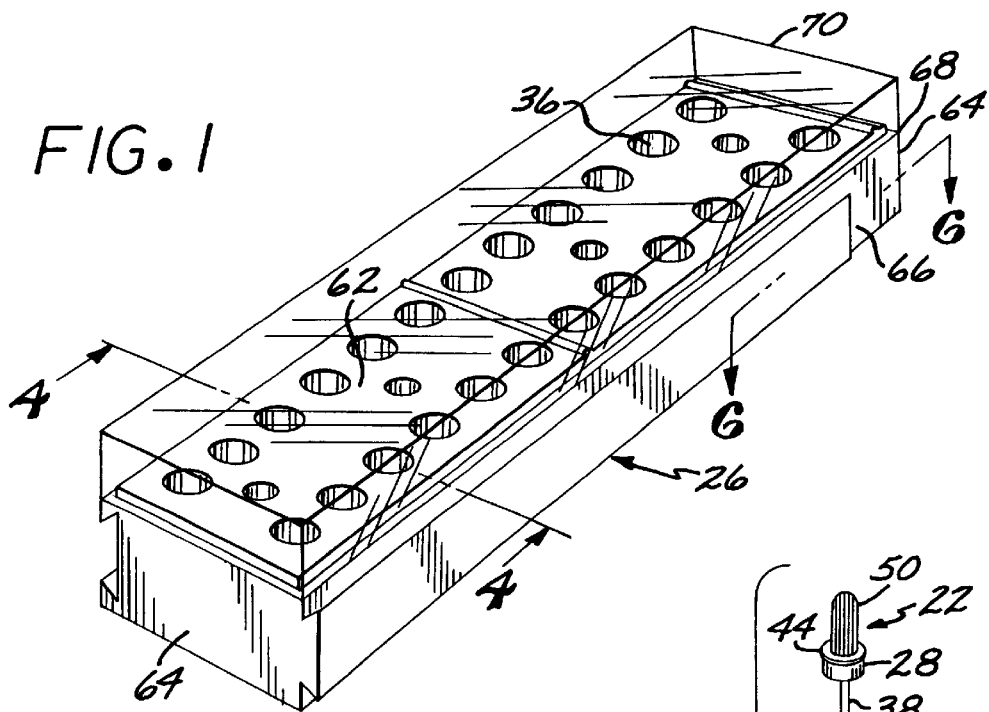
FIG. 1 is a perspective view of a tray apparatus for holding allergen vials of the allergy testing apparatus of the present invention.

In the following detailed description, like reference numerals will be used to refer to like or corresponding elements in the different figures of the drawings. The allergy testing apparatus of the present invention is embodied in an apparatus 20 (FIG. 5) for testing a patient's reaction to one or more allergens by applying allergen under the skin of a patient. More particularly, one aspect the invention includes, generally, a set of applicator picks 22 (FIG. 2) for applying allergen under the skin of the patient, a set of vials 24 (FIG. 2) which contain allergen specimens and into which the applicator picks fit, and a tray 26 (FIG. 1) which holds the vials and applicator picks during testing and storage. Many novel features have been included in the design of the applicator pick, vial and tray which make use of the apparatus much more convenient and efficient. For example, the applicator pick incorporates a downwardly opening, integral, enlarged in diameter cup shaped plug 28 (FIGS. 2 and 7) which fits into the large open mouth 30 of the vial, thereby significantly reducing the number of parts required and allowing the vial to have a wider mouth opening for easy access. The applicator pick also includes improved long slender conically shaped tines 32 (FIG. 9) at its bottom which facilitate skin puncture and provide effective application of allergen. The applicator pick is versatilely designed with the tines being relatively long and narrow so as to be used in either the puncture or abrasion modes. The vial, being scaled at its top by the plug of the applicator pick, has a wide mouth opening for easy insertion of the applicator pick and is provided at its bottom with a sump 34, referred to in FIG. 7, which ensures efficient use of substantially all of the expensive allergen. The tray into which the vials and applicator picks arc held is configured such that two or more trays can be attached together, providing significantly enhanced flexibility and convenience to the technician at nominal cost, and is further provided with an optional clear plastic cover making storage more convenient.

The picks are configured centrally with the large diameter cup shaped plugs 28 for removable receipt in the respective vial mouths 30, and have downwardly depending narrow stems 38 tapering to a diameter of about 0.16 inches at their bottoms and having a draft of 1°. Such stems are formed at their bottom extremities with a circular pattern of downwardly depending sharp, generally conically shaped, pointed tines 32 (FIG. 7) for, in the puncture test, penetrating under the epidermal layer of human skin. The tines serve primarily two functions. First, they provide a capillary action by increasing the surface area at the bottom of the stem, thereby loading the desired amount of allergen to the bottom of the applicator pick. This ensures that a proper dosage of allergen will be administered to the patient during any given application. Secondly, the tines are used to apply the allergen into the skin of the patient. Because they are of a selected length and sharply pointed, the tines can pierce the skin of the patient, thereby allowing the predetermined quantity of allergen suspended from the tip of the applicator pick to be deposited into the patient's skin for effective reaction in the patient.

The relatively long conical shape of the tines 32 (FIG. 9) is optimum for use in either the puncture or abrasion modes. This is because the conical shape provides a sharp point while minimizing the surface area of the tine. By minimizing the cross section of the tines, providing a circular shape and a selected length, the resistance to penetration of the tine by the patient's skin is reduced. The conical shape of the base portion of the tines also provides symmetrical structural rigidity about the entire radius of the tine, thereby uniformly resisting bending loads in any direction. The conical shape further provides a diameter which increases linearly from the tip portion toward the base of the respective tine. When the applicator pick is used in the abrasion mode, a force is exerted near the tip of the tine perpendicular with the longitudinal axis of the tine. This force causes a bending stress in the tine which increases linearly with distance from the tip of the tine. Having a diameter which increases linearly down the length of the tine causes the base portion of the tine to possess a stiffness which is directly proportional to the linearly increasing bending stress along the length of the tine. The tines terminate at the flat bottom wall 40 of the stem 38 (FIGS. 8 and 9), creating a stop to limit penetration of the tines. In this way each of the tines can easily be inserted into the patient's skin to a precise, predetermined depth.

Figure 7:
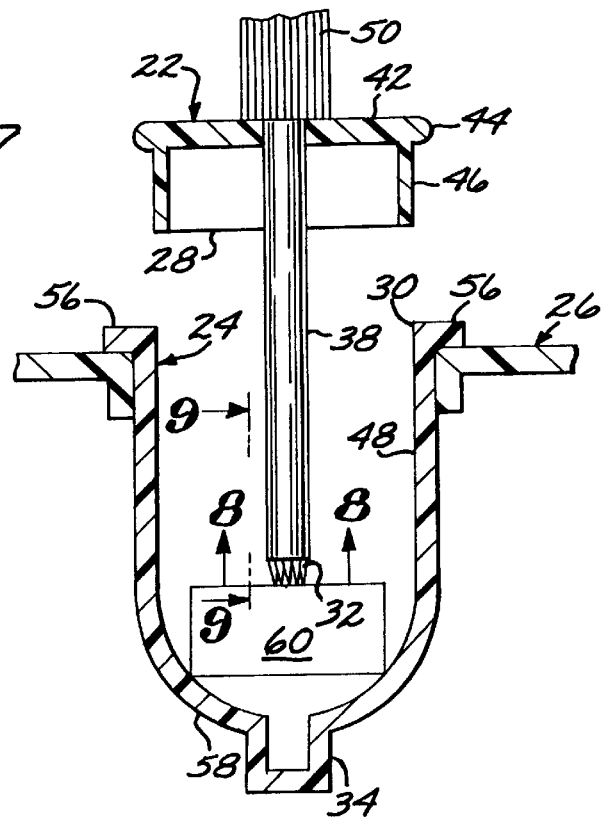
FIG. 7 is a transverse sectional view, in enlarged scale, taken along line 7—7 of FIG. 5 showing the applicator being inserted into the vial while the vial is installed in the tray.

Referring to FIG. 7, at the top of the narrow stem 38 of the applicator pick 22 and integral therewith, is formed a downwardly opening cup shaped plug 28 which is configured with an outer periphery to fit snugly into the top of the allergen vial 24, securely sealing the allergen therein. The plug 28 consists of a circular horizontal disk 42 defining a top wall which is radially and concentrically disposed about the longitudinal axis of the shaft 38 and configured with a parametrical annular lip 44. Extending downward from the outer edge of the disk is a cylindrical sleeve 46. The sleeve is configured to form a free sliding fit within the collar 48 defining the mouth of the vial 24. By constructing the cap integrally with the applicator pick, greater efficiency is achieved. Projecting above the cup shaped plug 28 is an upstanding handle 50 referred to in FIG. 2. The handle is knurled or ribbed to allow easy gripping by the technician and is of sufficient diameter to make the applicator pick easy to manipulate.

With reference to FIG. 7, the lip 44 projects radially outwardly about the entire perimeter of the plug 28 to define a limit ring projecting radially outwardly beyond the cylindrical sleeve 48. When the applicator pick and its cap are fully inserted into the vial 24, the lip 44 nests on the top edge of the vial. In this way, the lip of the plug 28 acts as a stop, allowing the applicator to be easily and consistently inserted the proper distance into the vial 24. By causing the applicator pick 22 to be inserted the proper distance into the vial, the tip of the applicator will be correctly placed in the bottom of the vial in a location which is optimal for collecting allergen but in which the tip will not contact the bottom wall of such vial.

Figure 8:
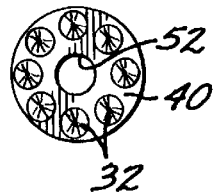
FIG. 8 is an end view, in enlarged scale, taken along line 8—8 of FIG. 7.
Figure 9:
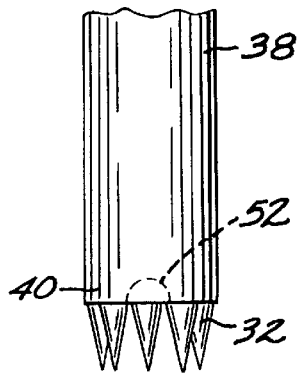
FIG. 9 is a side view, in enlarged scale, taken along line 9—9 of FIG. 7.

In the preferred embodiment referred to in FIGS. 8 and 9, the applicator pick 22 can include from six to eight conical tines 32 but preferably includes eight tines 32 arranged in a circular pattern about the longitudinal axis of the applicator pick. In the center of the circular pattern, a downwardly opening concave allergen cup 52 (FIG. 8) is formed in the bottom wall 40 of the stem 38. The tines cooperate to provide a capillary action causing allergen to adhere to the tip of the applicator pick 22 and the cup 52 further increases the capillary action. The tines 32 can be arranged in different patterns but in the preferred embodiment are disposed in a circular pattern about the central axis of the pick 22 in a pattern defining a circle having a 0.05 inch radius. The individual tines may be of various lengths such as from 0.050 to 0.1 inches, but are preferably about 0.31 inches in diameter at their respective bases and 0.07 inches long to facilitate penetration of the epidermis. Likewise, the cup 52 which can be of various depths is preferably configured with a radius of 0.03 inches and a depth of 0.01 inches.

Figure 2:
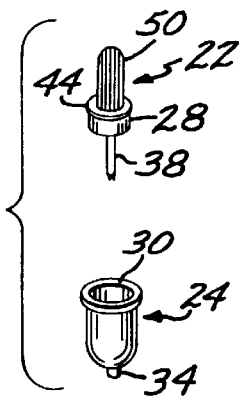
FIG. 2 is a perspective view of an allergen vial and applicator pick of the present invention.

Referring to FIG. 2, the vial 24 is cylindrically shaped and designed to fit within one of several wells 36 which are provided in a tray 26 as referred to in FIG. 1. With reference to FIG. 7, the vial is formed with the upwardly opening collar 48 into which the sleeve 46 of the plug 28 of the applicator pick 22 tightly fits and has a generally curved, closed bottom. Extending radially outwardly from the top edge of the collar is a lip 56 which nests upon the top surface of the tray to act as a stop to support the vial. The collar 48 forms a large interior diameter defining a mouth 30 of 0.39 inches to facilitate ease of insertion of the applicator pick. The stem 38 of the applicator pick 22, having a much smaller diameter than the inner diameter of the vial, can be easily inserted into the vial without requiring a high degree of manual dexterity on the part of the technician.

With continued reference to FIG. 7, the curved bowl shaped bottom wall of the vial 24 is provided with a downwardly depending small cylindrical sump 34 configured for complemental receipt of the bottom end of the pick 22 and into which the allergen collects. When the applicator pick 22 is fully inserted into the vial, the tip of the applicator will be disposed within the sump, thereby allowing allergen contained within the sump to adhere to the tip of the applicator. Use of the sump assures that substantially all of the expensive allergen will be effectively used and further assures that the last application from the vial will deliver the proper amount of allergen for delivery to the patient.

Referring again to FIG. 7, the exterior wall of the vial is provided with a frosted patch 60 of roughened texture which can be written on using a standard marker. This allows the technician to easily label the vial, further increasing convenience to the technician.

Figure 3:
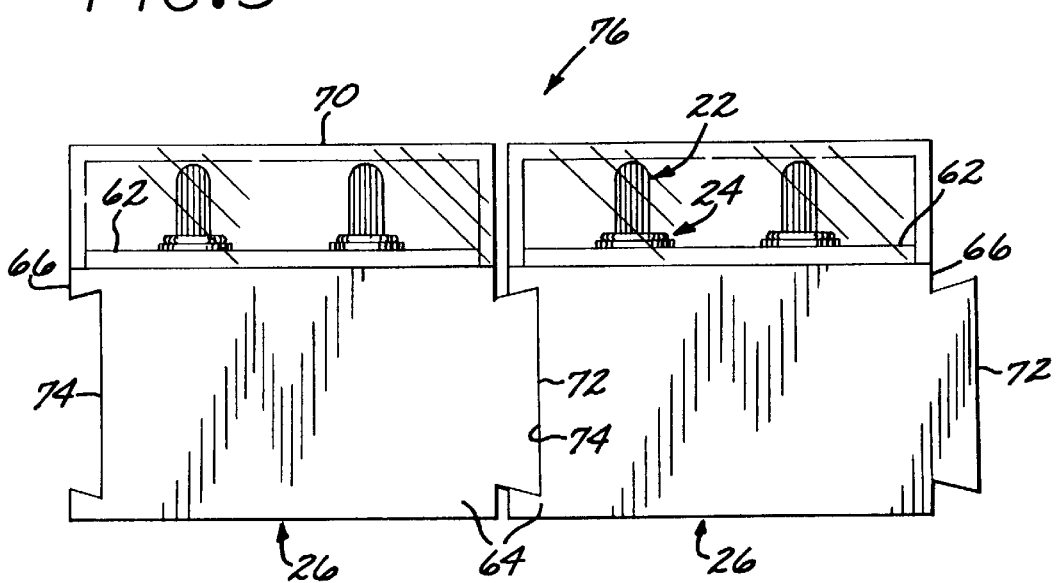
FIG. 3 is a left end view, in enlarged scale, of a pair of tray apparatus, as shown in FIG. 1, assembled together showing the pick of FIG. 2, in enlarged scale.
Figure 4:
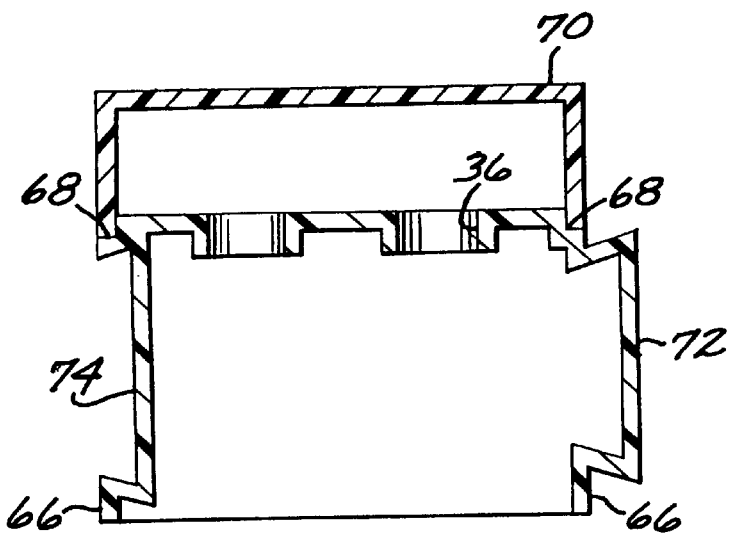
FIG. 4 is a transverse sectional view, in enlarged scale, taken along line 4—4 of FIG. 1.

Referring to FIGS. 1 and 3, the tray 26 is generally in the form of a block shaped, open bottom plastic shell having a flat rectangular top wall 62, opposite end walls 64 and elongated side walls 66. Formed integral with the top wall are a plurality of upwardly opening cylindrical wells 36 for receiving the vials 24 of allergen. For the purpose of illustration, I show two rows of twelve wells 36. However, in practice, I have found that a set of 20 wells 36 arranged in two rows of ten each provides for holding a sufficient number of vials for many applications. The wells extend only slightly downward from the top of the tray 26. It will be appreciated that in the event it becomes necessary to change a vial the technician can push up on its bottom wall to dislodge it for removal. The tray is formed about its upper periphery with an outwardly and upwardly opening notch 68 (FIGS. 1, 4 and 5) for complemental receipt of the lower edge of a box-like transparent, downwardly opening lid, generally designated 70. The tray and lid combine to provide, even with the wells filled with vials, the overall combination with a brick-like shape so such vial filled trays and lids may be easily stacked for storage and shipping. The trays can also be stacked and immobilized without the lid.

Figure 6:
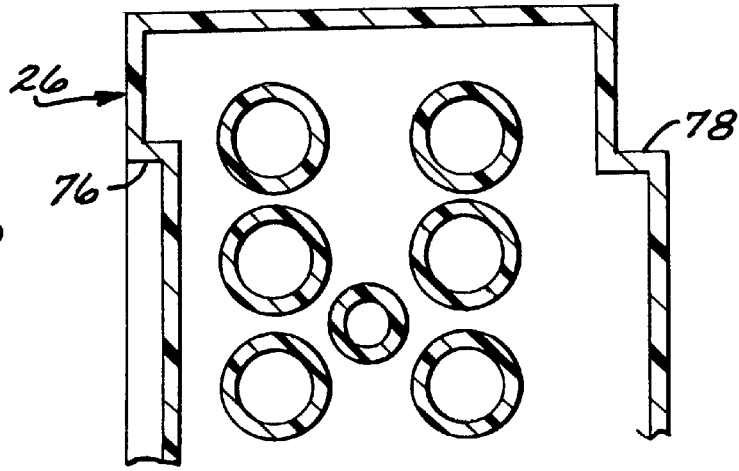
FIG. 6 is a sectional plan view, in enlarged scale, taken along line 6—6 of FIG. 1.

The tray 26 preferably includes releasable couplers on its opposite sides for coupling a selected number of such trays together in side by side relationship. In one embodiment such tray is formed in its opposite sides with a respective longitudinal coupling tongue 72 and a groove 74 to facilitate coupling two or more trays together to form a larger kit, generally designated 76, shown in FIG. 3. The tongue and groove are formed with a dovetail cross section for a sliding, interlocking relationship. Referred to in FIG. 6, the grooves 74 are open on one end of the tray but stop short of the other end, thereby providing a groove end 76 to be engaged by a stop 78 formed at one end of the tongue 72 a short distance from the corresponding end wall of such tray, to limit sliding of such connecting tongue rail to maintain such trays aligned in flanking relationship. In this way, the technician can slide two trays together until the stop 78 of one tray reaches the groove end 76 in the second tray at which point the two trays will be perfectly adjacent and securely coupled to one another. The capability of coupling two or more trays together is an important advantage to the technician. If a patient requires use of only a small number of allergens, then the single tray can be used. However, if a patient requires testing of a greater number of allergens, the kit can be expanded to include all of the required allergens in one convenient kit for rapid and efficient use to apply all the allergen prescribed for the particular patient.

It will be appreciated by those skilled in the art that the trays 26 and lid 70 (FIG. 1) can be conveniently and inexpensively constructed of thermoplastic material. Likewise, the vial 24 and applicator pick 22 can be molded of thermoplastic using an injection molding process.

Figure 5:
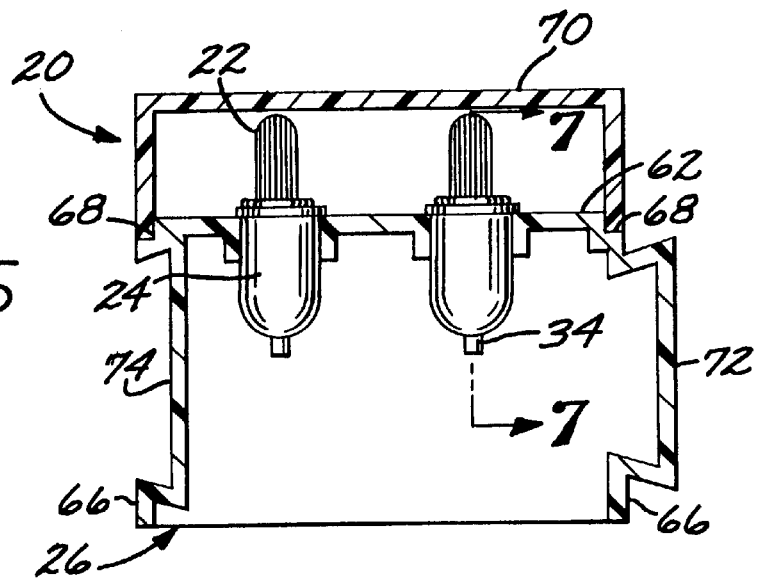
FIG. 5 is a transverse sectional view similar to FIG. 4 showing a pair of applicators inserted, taken along line 4—4 of FIG. 1.

In operation, the trays 26, vials 24, applicators 22 and lid 70, referred to in FIG. 5, may be shipped from the factory to the office of the doctor or laboratory technician. When a patient is to be treated with, for instance, approximately 24 or less allergens, only a single tray may need to be used. When a patient is to be tested for allergenic reaction, the allergenic extracts or allergens to be tested on the patient may be selected. Vials 24 may be inserted in the respective wells of the tray and filled with the selected allergen. To facilitate identification of the vials of allergen, the operator may label the allergen vials by writing an identification or code on the frosted patch 60 of each of the selected vials using a pen or other standard writing implement.

In the event the technician elects to apply a number of allergens greater than that for the number of wells in a particular tray 26, it is convenient to merely couple two or more trays together, as shown in FIG. 3, to provide the desired number of vials carried in the various wells 36. In this fashion, assuming the technician sought to administer, for instance, 38 different allergens, two trays would be coupled together by sliding the tongue 72 of one tray into the open end of the dovetail groove 74 of the adjacent tray to the extent permitted by groove end 76 and stop 78 (FIG. 6) thus assuring longitudinal alignment of the respective trays to provide a pair of modules having a total capacity of, for instance, 44 vials. Assuming the technician proceeds with the 38 different vials selected, the wells of one full tray 26 may be filled with respective vials and 16 wells of the second tray may likewise be filled with vials. The vials will be typically prefilled with allergen before the procedure is commenced so that the technician can quickly and efficiently remove the picks from the respective vials 24 and administer the allergen as described hereinabove to thereby provide for treating the patient in the minimum amount of time and thus minimize the period of time to which the patent is subject to the trauma and stress associated with any concern which may be raised about the overall procedure.

As the technician then treats the patient, the picks 22 (FIG. 3) may be withdrawn in progression from the respective vials 24. As the respective stems 38 (FIG. 2) are withdrawn from the allergens in the respective vials, the capillary action of the allergens will cause a selected quantity of such allergens to adhere to the surfaces of the respective tines 32 (FIG. 9) and bottom wall 40 of the stem 38 and within the confines of the allergen cup 52 (FIGS. 8 and 9). In this regard, it will be apparent to those skilled in the art that allergens have generally the same viscosity and, within reason, the same general capillary characteristics, such that the desired quantity of allergen will remain adhered to the tip of the stem as it is removed from the vial. The technician may then apply the allergen beneath the patient's skin by pressing the end of the applicator pick against the patient's skin using either the puncture or abrasion techniques.

It will be appreciated that this option of utilizing the individual pick for administration of the allergen by either a puncture method or an abrading or scarifying method is of great advantage. Referring to FIGS. 7, 8, and 9, for the puncture method the technician will merely move the pick 22 over the skin with the residual allergen fluid adhered by capillary action to the surfaces of the tines 32, bottom wall 40 and cup 52 and pressing the stem inwardly to cause the points of such tines to puncture the skin in a circular pattern so that further inward pressing will serve to introduce the quantity of allergen held thereon some 0.07 inches beneath the exterior surface of the patient's skin to penetrate beneath the relatively tough epidermis. Since the quantity of allergen and maximum depth of the puncture is already predetermined by the length of the tines, the depth of penetration and amount of allergen introduced is limited. Consequently, this administration can be performed by a technician with a minimal amount of experience and understanding of the medical ramifications thereof. It will be appreciated that the multiple long thin tines will serve to not only cooperate together in carrying the desired quantity of antigen but will puncture small diameter thin puncture holes to be effective in introducing the necessary quantity of antigen, while provoking only a slight skin irritation in the patient, far less than would be the case for one or more larger diameter prongs or tines. In the event the patient proves to have unusually tough skin or skin otherwise not susceptible to easy puncture, there remains a ready option.

The technician may resort to what is known as the "scratch test" where the skin is typically abraded by a scarifying device. The applicator of the present invention can be utilized by even the most inexperienced technician. In this approach, the points of the tines 32 (FIG. 9) are only slightly penetrated into the skin surface and the technician may turn the handle 50 (FIG. 2) to rotate such stem about its longitudinal axis causing the points to scratch the skin surface, making small cuts therein for positive introduction of the allergen carried on such tines. Once the patient is screened by either the above described puncture or scratch technique without a reaction, an injection technique may be carried out with a hypodermic needle or the like to inject larger quantities of allergen beneath the skin.

The used pick 22 referred to in FIG. 2 will then be discarded and a new pick selected for each of the vials of the tray and inserted into the vial at the end of the test to act as a stopper to maintain the biological cleanliness of the allergen until the next application for the subject patient or subsequent patient. It will be appreciated that insertion of the applicators in the wide mouth 30 of the vials is facilitated by the relatively small diameter of the stems 38 which serve to essentially lead the applicator into such vial as it is lowered, as shown in FIG. 7, to thus maintain the pick somewhat centered in the vial so as to tend to register the skirt 46 of the plug 28 concentrically with the mouth 30 so that the technician may quickly and positively register such plug into sealing position for positive sealing thereof. The procedure will then be repeated for each of the picks in the vials positioned in the tray 26 (FIG. 5). When all of the picks have been discarded, the technician will know that this particular treatment of the patient has been completed.

Before the tray is stored, the technician inserts new sterile picks 22 (FIG. 2) into the respective vials 24 so that the respective mouths 30 of the vials will be closed by the respective plugs 28 of the new picks 22. For storage, the clear plastic cover 70 (FIG. 5) may be placed onto the tray to allow the assembled allergy testing kits 20 to be easily stacked, significantly saving storage space.

Figure 10:
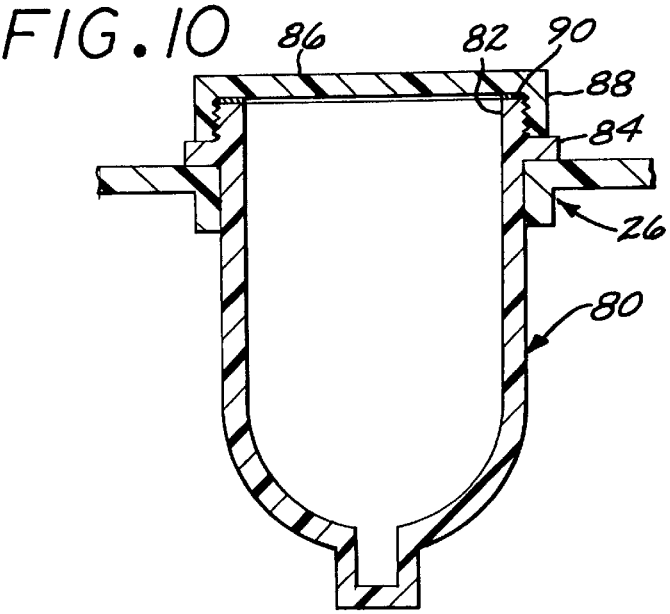
FIG. 10 is a sectional view similar to FIG. 7 but showing an optional vial with a threaded cap on the open mouth.

In an alternate embodiment, shown in FIG. 10, a vial 80 is provided, substantially the same as the vial referred to in FIGS. 1–7 but including a rim or skirt 82 projecting upwardly above the lip 84 and threaded on its exterior for engagement with the cylindrical wall of a closure cap, generally designated 86. The cap is conveniently constructed of plastic and formed with a cylindrical stub wall 88 formed on its interior with mating threads. An annular compression seal 90 may be frictionally held within the cap 86 for sealing against the annular top edge of the vial 80.

In operation, it will be appreciated that the vial 80 of FIG. 10 may be loaded with an allergen and the cap 86 screwed thereonto in tight sealing relationship so that the presterilized vial may be maneuvered about, stored, or shipped with its allergen contained therein and the cap in place. When the technician is then to gain access to the vial for utilizing the allergen, the cap 86 may be unscrewed and discarded. The pick 22 (FIG. 7) may then be inserted in place to move the plug 28 into sealing relationship with the mouth of the vial.

Figure 11:
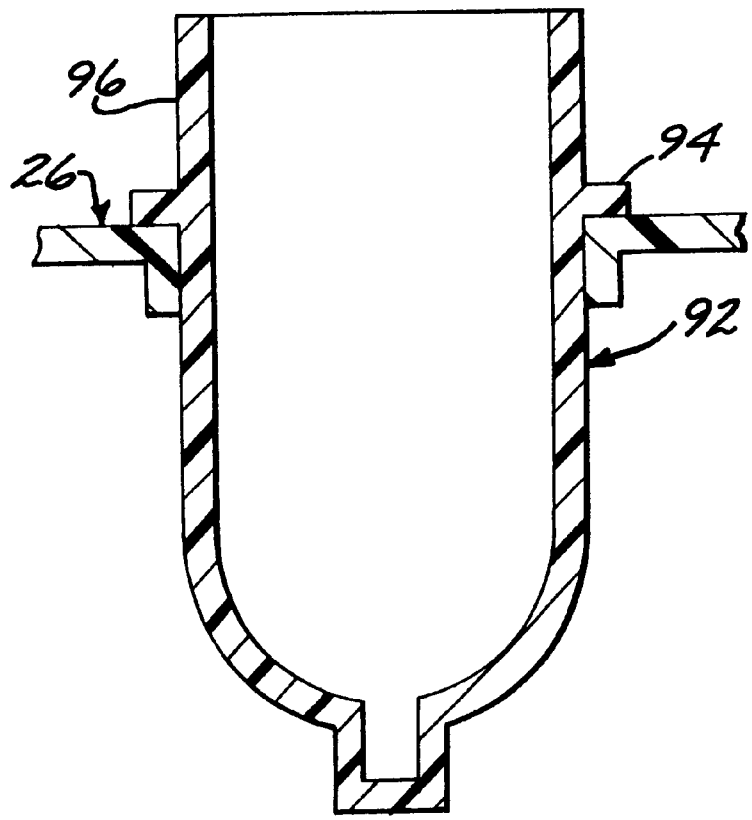
FIG. 11 is a sectional view similar to FIG. 7 showing a third embodiment of the vial.

In another alternate embodiment, referred to in FIG. 11, a vial 92 is provided which is similar to the vial 24 referred to in FIGS. 1–7 except that it projects vertically above a nesting lip 94 to define a cylindrical hand grasp rim 96.

In use, this embodiment allows convenient removal and interchange of vials 92 within a tray 26 referred to in broken sectional view in FIG. 11. If the technician desires to change the vials in a tray to accommodate the needs of a patient, the vial can be easily removed by grasping the rim 96 between the technician's thumb and index finger. This embodiment obviates the need to force the vial up from beneath, greatly increasing convenience to the technician.

Figure 12:
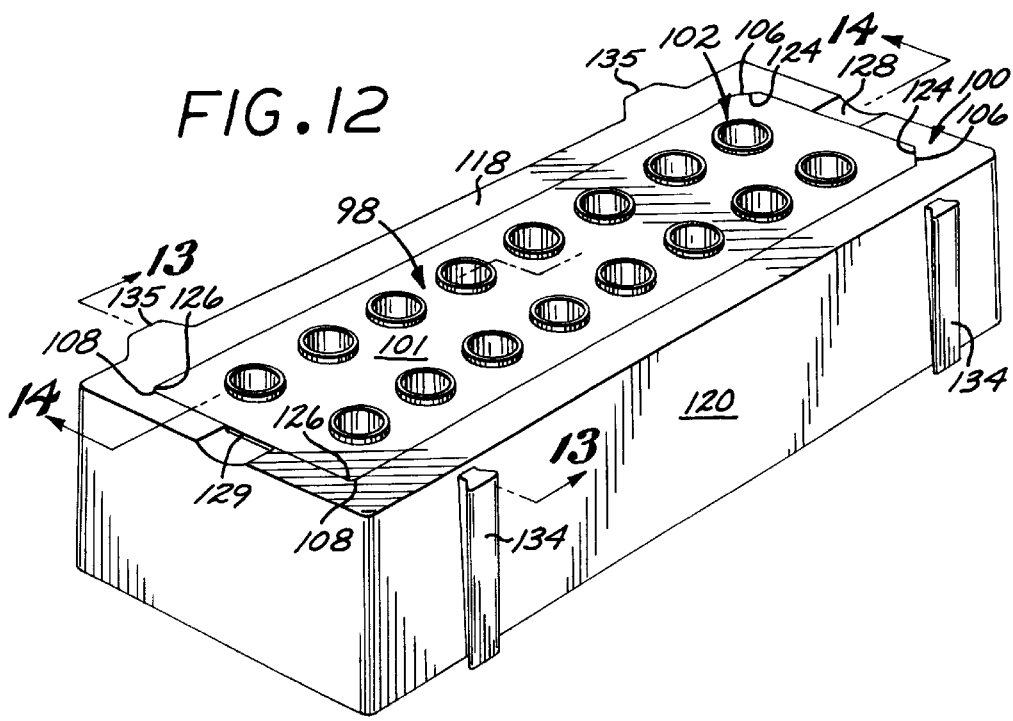
FIG. 12 is a perspective view of an alternate embodiment of a tray apparatus embodying the present invention including vials.
Figure 13:
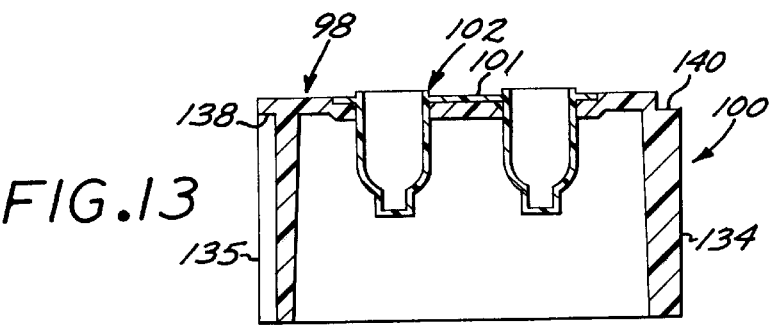
FIG. 13 is a transverse sectional view, in enlarged scale, taken along line 13—13 of FIG. 12.
Figure 14:
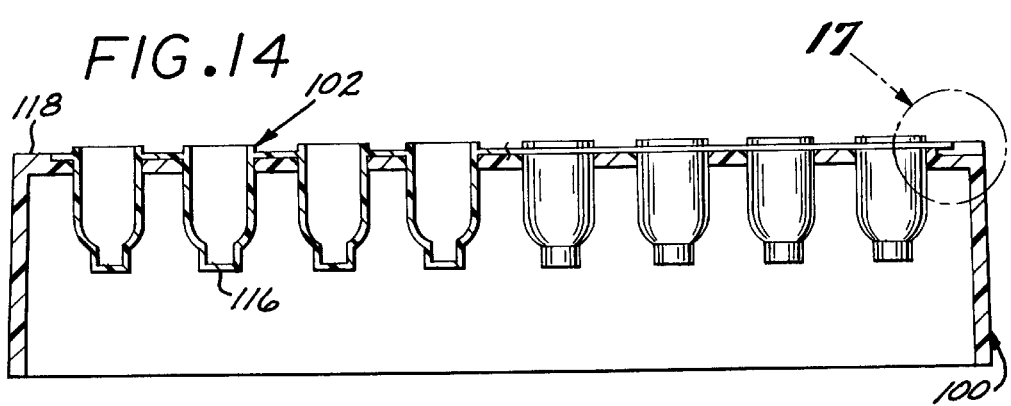
FIG. 14 is a longitudinal partial sectional view, in enlarged scale, taken along line 14—14 of FIG. 12.
Figure 23:
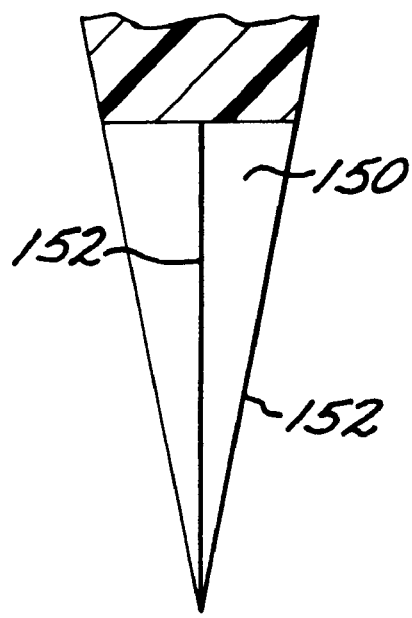
FIG. 23 is a view taken from circle 23 of FIG. 21, in enlarged scale.
Figure 24:
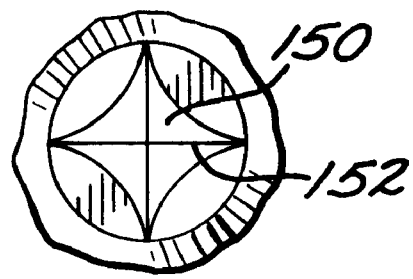
FIG. 24 is a bottom plan view taken from line 24—24 of FIG. 23.

The embodiment of the allergen applicator shown in FIGS. 12–24 is similar to that shown in FIGS. 1–11 and includes, generally, a well strip 98 configured for receipt within the top of a tray 100 (FIG. 12). The well strip includes a set of upwardly opening wells, generally referred to as 102 (FIG. 12), which are configured at their tops for receipt of a set of applicators, generally referred to as 104 (FIG. 19).

With reference to FIG. 12, the well strip 98 is constructed of plastic and is in the form of a flat rectangular plate 101 about 0.04 inches thick, integrally formed with the wells 102. I have found that in use, a well strip having 20 wells in two rows of 10 each provides a preferable configuration, providing both a sufficient number of wells for most applications and a manageable size which can be easily manipulated. However, for this example, I show two rows of 8 for a total of 16. The well strip is configured at the corners of one end with orientation tabs 106 in the form of chamfers designed for mating relationship within the tray 100, while the opposite end is formed with rounded corners 108 (FIG. 1).

With reference to FIG. 22, the open tops of the wells 102 extend beyond the top of the well strip to form stub walls defining sealing lips 110. The wells pass through the plane of the strip forming cylindrical collars 112 and terminate in rounded bottom walls 114. The bottoms of the wells terminate in cylindrical sumps 116 which serve to collect allergen when little allergen remains in the vial, thus assuring efficient use of substantially all of the allergen.

With reference to FIG. 12, the tray 100 is also constructed of plastic and is generally block shaped and formed with a rectangular top wall 118 with side walls 120 extending downwardly from the edges thereof. The well strip 98 fits into a rectangular recess 122 (FIG. 15 and 16) formed in the top of the tray. The recess is provided at one end with chamfered corners 124 (FIG. 12) and at its opposite end with rounded corners 126 formed to mate with respective oppositely disposed chamfered orientation tabs 106 and rounded corners 108, respectively, formed in either end of the well strip, thereby ensuring the correct orientation of the well strip within the tray. The top of the tray is further provided at each end with a finger slot 128 (FIGS. 12 and 17)) in the form of a notch having a depth greater than the thickness of the well strip, extending from the end of the tray to a point beyond the adjacent end of the recess. The finger slots provide access to respective finger tabs 129 formed by the respective opposite ends of the strip to facilitate convenient removal of the well strip by simply placing a fingernail or implement within each slot to reach beneath the respective tabs 129 to lift the strip out of the tray.

With reference to FIG. 16 the recess 122 formed in the top 118 of the tray 100 of the alternate embodiment includes well receiving holes 130 through which the wells 102 fit when the well strip 98 is installed in the tray. The wells have beveled upper edges 132 which assist installation of the well strip by deflecting the wells into proper position in the well holes when the well strip is slightly misaligned during installation.

With continued reference to FIGS. 15 and 18, a pair of vertical rails 134 formed on one side of the tray, configured for mating relationship with a pair of channel housings 135 defining channel tracks 136 (FIG. 13) on the opposite side of the tray, allow one tray to adjoin with another by sliding the rails of one tray vertically into the channels of the other tray. The rails and channels mate in dove-tail fashion and the channel housing is provided with a closed upper end 138 (FIG. 13) which engages the upper end 140 of the rail providing a stop to limit further movement of the rail within the channel when the trays are flush with one another as illustrated in FIG. 15.

With reference to FIG. 19, an alternate embodiment of the applicator pick generally referred to as 104 includes a downward depending tapered stem 142 terminating at a flat bottom 144 (FIG. 21). A set of generally conical thin tines 146 having slender pyramidal tips 148 extend from the bottom of the stem in a symmetrical, circular pattern. The pyramidal shape at the tip of each tine provides flat upwardly and outwardly diverging facets 150 (FIG. 23 and 24) which meet to form edges 152 to promote cutting of the patient's skin during initial puncture allowing the tip of the tine to more easily pierce the patient's skin. The pyramidal shape also facilitates manufacture of the applicator by aiding in removal of the tine from a mold. While the preferred embodiment of the pyramidal tip includes four facets, other pyramidal shapes having at least three facets can similarly provide the advantageous cutting effect. This pyramidal tip smoothly joins a frusto conical remainder of the tine, which constitutes the majority of the length of the tine. Once the tips of the tines have initially pierced the patient's skin, the frusto conical shape of the remainder of the tine optimally facilitates further insertion of the tine by minimizing the surface area in contact with the patient's skin and correspondingly minimizing frictional resistance to further insertion of the pick. The frusto conical configuration of the remainder of the tine provides uniform resistance to bending stresses throughout the majority of the length of the tine, increasing at the portions of the tine closest to the base where the bending stresses on the tine will be greatest when the pick is used in the abrasion mode.

While several configurations of tines could provide satisfactory results, I have found that eight tines 146, disposed in a circular pattern about the bottom of the stem, provide a preferable configuration for use in both the puncture and abrasion modes. Disposing the tines in a circular pattern allows the tines to abrade the patient's skin in a circular pattern when the technician twists the applicator about its axis. While the tines could be of various lengths and widths, I have found that tines having an overall length of 0.070 inches from base to tip and a width of 0.031 inches at the base provide advantageous sharpness as well as bending resistance and moldability. The pyramidal tip of such a tine should make up the last 0.030 inches at the tip of the tine. I have found that the picks may be injection molded from polyacetal sold under the trademark CELCON® or DELRIN®.

I have found that such tines should have an overall length greater than 0.05 inches to, in the puncture test, reach under the epidermis but not greater than about 0.1 inches to avoid excessively deep penetration which would add to the patient's trauma. The base of the stems should be at least 0.020 inches wide to afford the necessary structural integrity but not more than about 0.045 so as to avoid an unduly large cross section puncture and consequent discomfort.

With reference to FIG. 21, the tines 146 surround a dome shaped, allergen cup 156 formed at the center of the flat bottom 144 of the stem 142. The allergen cup opens downwardly, having a depth of 0.01 inches and a radius of 0.065 inches. The allergen cup serves to increase the surface tension at the bottom of the stem, creating a capillary effect in order to cooperate with the surface of the tines to hold a predetermined quantity of allergen upon withdrawal of the applicator from a well 102 (FIG. 22) for application to a patient. As will be appreciated by those skilled in the art, for the screening test, whether it be by the scratch or puncture technique, the quantity of allergen should be about 0.1 cc or about $\frac{1}{20}$th of that utilized in an intradermal technique. I have found that with this combination, the pick of the invention is effective to repeatedly carry about 0.1 cc of antigen from the respective wells.

With reference to FIG. 19, the applicator pick 104 includes a top 158 in the form of a disk extending radially from the upper portion of the stem 142 of the pick. The radial extremity of the disk turns downward to form a circumferential flange 160 (FIG. 22) for sealing engagement with the sealing lip 110 at the top of the well 102 in which it is inserted. Although described for use with the well (FIG. 23), it will be appreciated that this pick embodiment 104 could also be used with the vial 24 (FIG. 2) of the previously described embodiment.

A cruciform collar 162 (FIG. 19) extends downward from the disk shaped top in the form of four vertical flanges 164 (FIG. 20) projecting radially from the stem at right angles to one another and dimensioned radially so as to fit slidingly and freely within the cylindrical collar 112 of the well 102 (FIG. 22). Such collar may, in practice, be constructed in the form of a cylindrical plug body loosely fit in a well 102.

Referring to FIGS. 8 and 22, a narrow cylindrical handle 166 extends upward from the disk shaped top 158, coaxial with the stem 142 so as to be conveniently gripped between the thumb and index finger, not shown, of the technician during use. The handle is supported by a cylindrical neck of relatively smaller diameter than the handle, extending a short distance from the top 158. The neck flares radially outward at its top to form a shoulder 122 serving as the bottom of the handle portion. The shoulder facilitates removal of the pick 104 from the well 102 by creating a surface against which to grip when pulling upward on the handle. Knurls or ribs 168 formed in the surface of the handle further facilitate gripping the handle during use.

As will be appreciated by those skilled in the art, the tray 100, well strip 98 and applicator pick 104 can be easily and inexpensively constructed of injection molded thermoplastic. The stem 142 of the pick is formed with a 10 draft which facilitates removal of the pick from a mold, not shown. The tray and well strip can also be formed by vacuum molding.

To use well strip 98, the physician may first install the well strip into the rectangular recess 122 of the tray 100, aligning the chamfered orientation tabs 106 of the well strip 98 with the chamfered corners 124 of the recess 122 to assure correct alignment, and then fill the wells 102 with the desired allergen. The technician may then install the applicator picks 104 (FIG. 20) into the tops of the wells to seal the allergen therein. The collar 162 will guide and hold the applicator pick in place within the well.

Should the physician wish to use a different set of allergens, he or she can simply remove the existing well strip 98 by lifting the tray from the finger tabs 129 to discard the entire strip and picks. The technician may then replace the well strip with another well strip previously loaded with the desired allergen. If more than 16 allergens are to be tested, the technician has the option of creating a larger test kit by sliding the rails 134 of one tray vertically into the channels 136 of another tray until the upper ends of the rails 140 stop against the closed upper ends of the vertical channel 136, thereby locking the two trays together.

When a physician undertakes to screen a patient, he or she may withdraw the individual applicator pick 104 from the bath of antigen in the respective well 102 causing the tines 146 and cup 156 to carry therewith about 0.1 cc of antigen. The applicator pick 104 can be either pressed directly down onto the patient's skin for use in the puncture mode to cause the sharp thin pyramidal points 148 to knife through the epidermal layer peeling the skin back to open the way for the conical remaining length of such tines 146. The tines 146 will thus serve to carry a great majority of the 0.1 cc of antigen thereon and cooperate with the cup 156 so that during puncture or scratching effective application of the antigen along the long slender surface will be accessed. The technician can press downwardly without concern over an excessively deep penetration since the tines themselves are only 0.070 inches long to reach just under the epidermis. Should the patient have unusually tough or thick skin, the technician can withdraw the tines so just the tip section remains in the outer skin layer. Then by rotating the pick about its own axis, the tine tip will scratch the skin depositing the particular allergen in the scratches to test for a reaction. For those allergens where there was symptoms of an extraordinary reaction, the technician might turn the patient over to the experienced medical doctor for an injection test where a hypodermic needle is employed to inject allergen under the skin to introduce a larger quantity of allergen. The physician may then examine the skin for symptoms of a reaction to form an opinion as to whether there might be any overaction should he or she proceed with the intradermal test.

From the forgoing it will be appreciated that the invention provides significant cost savings while including features which greatly enhance convenience and versatility. The disclosed use and arrangement of conical tines with pyramidal tips and use of a central bore will create the most effective and versatile applicator pick. In addition, the provision of a pyramidal tip on the conical tines can further enhance the effectiveness of the tines. It will also be clearly evident that the use of a cap integral with an applicator pick provides added economy and convenience by significantly reducing the number of parts required as well as by allowing the applicator pick to be inserted into the relatively large opening in the top of the vial. Convenience is also achieved by obviating the use of a knife or other tool to open the vial. It will also be appreciated that the invention provides greater flexibility by allowing a large number of allergens to be included in one kit by fastening several trays together. Finally, providing a clear cover for the tray makes storage more convenient. While several particular forms of the invention have been illustrated and described, it will also be apparent that various modifications can be made without departing from the spirit and scope of the invention.

What is claimed is:

1. A plastic antigen pick device comprising:
   a plastic shaft formed with an upstanding handle and a downwardly depending, reduced-in-cross-section stem, terminating in a bottom end for disposal in a bath of allergen; and
   a plurality of elongated thin abrading tines tapered in respective sides thereof to project downwardly a distance greater than 0.5 mm from said bottom end and terminating in respective sharp puncture points having upwardly and outwardly angled facets to puncture through the skin of a human patient.

2. The device of claim 1 wherein:
   said stem is formed with a central axis; and
   said tines are disposed in a symmetrical pattern about a line extended from said axis.

3. The device of claim 1 for use with an allergen having a predetermined viscosity and that includes:
   capillary means on said bottom end of said stem for, upon being withdrawn from said bath, retaining a predetermined quantity of said allergen.

4. The device of claim 1 wherein:
   said stem is formed with sides that taper downwarldy and upwardly along the length thereof.

5. The device of claim 1 wherein:
   said tines are at least partially conically shaped.

6. The device of claim 1 wherein:
   said bottom end of said antigen pick is formed with a centrally disposed, downwardly opening measuring reservoir.

7. The device of claim 1 wherein:
   said tines are formed with a base of substantially 0.032 inches and a length of substantially 0.070 inches.

8. The device of claim 1 wherein:

said stem and tines are one piece.

9. The device of claim 1 for use with a vial formed with a collar having a relatively large interior cross section, and that includes:

a plug mounted on said stem disposed below said handle and formed with a cross section to be received complementally in said relatively large interior cross section of said collar.

10. The device of claim 9, wherein:

said plug is formed with a downwardly opening groove for complemental receipt over said collar.

11. The device of claim 1 wherein:

said plug includes downwardly projecting radial fins configured to be complementally received in said collar.

12. The antigen pick device as set forth in claim 1, wherein:

said tines are formed with tips configured with a plurality of identical flat facets diverging upwardly and outwardly from the respective points.

13. The device of claim 12 wherein:

said tips are formed with three or more upwardly and outwardly angled facets.

14. The device of claim 13 wherein:

said tips are pyramidal shaped.

15. The device of claim 12 wherein:

said tips are substantially 0.030 inches long.

16. The device of claim 15 wherein:

said tines are substantially 0.070 inches long.

17. A set of plastic antigen picks for use with a tray apparatus including a plurality of upwardly opening vials, each pick including:

a shaft formed with a plug for engaging a respective one of said vials, a handle rising upwardly from said plug and a stem depending downwardly therefrom to define a longitudinal axis, said stem having a bottom end defining a stop, said pick further including a plurality of tines arranged in a uniform pattern about an extension of said longitudinal axis and projecting more than 0.5 mm from said stop to define respective points, said picks being disassociated from one another.

18. A set of antigen picks as set forth in claim 17 wherein:

said tines are formed with bases no more than 0.020 inches across.

19. A set of antigen picks as set forth in claim 17 wherein:

the lateral sides of said tines angle laterally inwardly in the direction toward said point.

20. A set of antigen picks as set forth in claim 17 wherein:

said stem and tines are integral.

* * * * *

UNITED STATES PATENT AND TRADEMARK OFFICE
CERTIFICATE OF CORRECTION

PATENT NO. : 6,077,229
DATED : June 20, 2000
INVENTOR(S) : Isadore Pitesky

It is certified that error appears in the above-identified patent and that said Letters Patent is hereby corrected as shown below:

Column 5, line 46, delete "scaled" and insert --sealed--;

Column 5, line 51, delete "arc" and insert --are--;

Column 10, line 11, delete "scaling" and insert --sealing--;

Column 11, line 25, delete "comers" and insert --corners--; and

Column 13, line 32, delete "comers" and insert --corners--.

Signed and Sealed this

Twenty-seventh Day of March, 2001

*Attest:*

NICHOLAS P. GODICI

*Attesting Officer*  *Acting Director of the United States Patent and Trademark Office*